United States Patent
Schmidt et al.

(10) Patent No.: US 6,692,578 B2
(45) Date of Patent: Feb. 17, 2004

(54) HYDROLYSIS OF BIOMASS MATERIAL

(75) Inventors: Andrew J. Schmidt, Richland, WA (US); Rick J. Orth, Kennewick, WA (US); James A. Franz, Kennewick, WA (US); Mikhail Alnajjar, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 98 days.

(21) Appl. No.: 09/792,906

(22) Filed: Feb. 23, 2001

(65) Prior Publication Data

US 2002/0117167 A1 Aug. 29, 2002

(51) Int. Cl.$^7$ .......................... C13K 13/00; C13K 1/02; C13K 1/04
(52) U.S. Cl. ......................................... 127/37; 435/105
(58) Field of Search ...................... 127/34, 37; 435/105

(56) References Cited

U.S. PATENT DOCUMENTS

| | | |
|---|---|---|
| 4,384,897 A | 5/1983 | Brink |
| 4,752,579 A | 6/1988 | Arena et al. |
| 5,221,357 A | 6/1993 | Brink |
| 5,366,558 A | 11/1994 | Brink |
| 5,424,417 A | 6/1995 | Torget et al. |
| 5,536,325 A | 7/1996 | Brink |
| 5,628,830 A | 5/1997 | Brink |
| 5,932,452 A | 8/1999 | Mustranta et al. |

FOREIGN PATENT DOCUMENTS

| | | |
|---|---|---|
| EP | 0159795 | 3/1985 |
| WO | WO 97/27293 | 7/1997 |
| WO | WO 98/56958 | 12/1998 |
| WO | WO 01/60752 | 8/2001 |

OTHER PUBLICATIONS

Adams, Canadian J. of Chemistry, 30:698–710, 1952.
Adams, Canadian J. of Chemistry, 33:56–67, 1954.
Barrier et al., in Biomass Energy Development, Wayne H. Smith (ed.), 587–600, Plenum Press, New York, 1985.
Bobleter et al., J. Carbohydrate Chemistry, 5(3):387–399, 1986.
Conner et al., Wood and Fiber Science, 18(2):248–263, 1986.
Dien et al., J. Industrial Microbiol. & Biotech., 22:575–581, 1999.
Doner et al., Cereal Chem., 75(4):408–411, 1998.
Feather et al., Adv. Carbohydrate Chem. Biochem., 28:161–224, 1973.
Garleb et al., J. Anim. Sci., 66:2650–2662, 1988.
Ghali et al., Starch, 1:23–26, 1984.
Gonzalez et al., Biotech. and Bioeng., 28:288–293, 1986.
Grethlein, Biotech. and Bioeng. Symp., 5:303–318, 1975.
Grohmann et al., Biotech. and Bioeng. Symp., 17:135–151, 1986.
Grohmann et al., Process Biochem., 32(5):405–415, 1997.
Gulati et al., Bioresource Tech., 58:253–264, 1996.
Harris et al., in Progress in Biomass Conversion, vol. 5, 101–141, Academic Press, Orlando, FL, 1984.
Hespell, Applied Biochem. and Biotech., 62:87–97, 1997.
Krishna et al., Carbohydrate Research, 158:253–261, 1986.
Lawford et al., Biotech. Letters, 14(5):421–426, 1992.
Leathers et al., Applied Biochem. and Biotech., 59:337–347, 1996.
Leathers et al., Process Biochem., 35:765–769, 2000.
Lee et al., Tappi Journal, 66(5):102–107,1983.
Mithel et al., Tappi Journal, 40(1), 1–4, 1957.
Moniruzzaman et al., Biotech. Letters, 18(8):985–990, 1996.
Moniruzzaman et al., Applied Biochem. and Biotech., 67:113–126, 1997.
Olson et al., J. Agric. Food Chem., 36:300–304, 1988.
Paszner et al., in 16$^{th}$ Conference of Energy from Biomass and Wastes, D.L. Klass, ed., Inst. Gas Technol., 629–664, 1992.
Philipp, Pure & Appl. Chem., 56(3):391–402, 1984.
Popoff et al., Carbohydrate Research, 22:135–149, 1972.
Rydholm, Pulping Processes, 124–127, John Wiley & Sons, New York, 1965.
Saha et al., Corn Utilization & Technology Conference Program Proceedings, St. Louis, MO, Corn Refiners Association, Inc. and National Corn Growers Association. Eds: Iannotti et al. (Jun. 1–3, 1998).
Saska et al., Biotech. and Bioeng., 45:517–523, 1995.
Scott et al., Analytical Biochem., 21:68–80, 1967.
Shibanuma et al., J. Appl. Glycosci., 46(3):249–256, 1999.
Sugawara et al., Starch, 9:335–337, 1994, no month provided.

(List continued on next page.)

*Primary Examiner*—David Brunsman
(74) *Attorney, Agent, or Firm*—Klarquist Sparkman, LLP

(57) ABSTRACT

A method for selective hydrolysis of the hemicellulose component of a biomass material. The selective hydrolysis produces water-soluble small molecules, particularly monosaccharides. One embodiment includes solubilizing at least a portion of the hemicellulose and subsequently hydrolyzing the solubilized hemicellulose to produce at least one monosaccharide. A second embodiment includes solubilizing at least a portion of the hemicellulose and subsequently enzymatically hydrolyzing the solubilized hemicellulose to produce at least one monosaccharide. A third embodiment includes solubilizing at least a portion of the hemicellulose by heating the biomass material to greater than 110° C. resulting in an aqueous portion that includes the solubilized hemicellulose and a water insoluble solids portion and subsequently separating the aqueous portion from the water insoluble solids portion. A fourth embodiment is a method for making a composition that includes cellulose, at least one protein and less than about 30 weight % hemicellulose, the method including solubilizing at least a portion of hemicellulose present in a biomass material that also includes cellulose and at least one protein and subsequently separating the solubilized hemicellulose from the cellulose and at least one protein.

20 Claims, No Drawings

OTHER PUBLICATIONS

Torget et al., *Applied Biochem. and Biotech.,* 28/29:75–86, 1991, no month provided.

Wayman, in *Cellulose Structure, Modification and Hydrolysis,* Young et al. (eds), 265–279, John Wiley & Sons, 1986, no month provided.

Weil et al., *Applied Biochem. and Biotech.,* 73:1–17, 1998, no month provided.

Whistler et al., *J. Am. Chem. Soc.,* 77:6328–6330, 1955, no month provided.

HYDROLYSIS OF BIOMASS MATERIAL

STATEMENT OF GOVERNMENT SUPPORT

This invention was made with United States Government support under Contract DE-AC06-76RL01830 awarded by the U.S. Department of Energy. The United States Government has certain rights in the invention.

FIELD OF THE INVENTION

The present invention relates to converting biomass material into commercially valuable intermediate or end products via hydrolysis.

BACKGROUND OF THE INVENTION

Biomass wastes and byproducts are generated by numerous manufacturing processes, municipality operations, and food and agricultural processing. Disposal of such biomass material is becoming an increasing problem. Agribusiness and chemical industries as well as government agencies have considerable interest in converting biomass material to higher value materials and in reducing the amount of biomass material requiring disposal. A need exists for an inexpensive, robust process for obtaining higher value products from biomass materials while simultaneously reducing the amount of biomass material.

Biomass materials that include hemicellulose and cellulose are particularly important since they are so prevalent. A common example of such material is the waste and byproducts from grain processing such as the stalks and leaves of the grain plant. Corn fiber, a byproduct of corn wet milling, and wheat stubble are two large volume biomass materials that include hemicellulose and cellulose. Corn fiber typically includes, approximately, 60 weight % fibrous material (primarily polysaccharides), 20 weight % starch, 10 weight % protein, 6 weight % ash, 2 weight % fat and smaller quantities of lignin and organic acids. The fibrous material component of corn fiber typically includes approximately 60 weight % hemicellulose, 30 weight % cellulose, 8 weight % galactan and 2 weight % mannan. Currently, corn fiber is supplemented with protein and sold as low value livestock feed. However, as noted above, a large component of corn fiber is hemicellulose. Livestock are unable to digest hemicellulose and, thus, much of the mass of corn fiber is of no nutritional value. A need exists for an inexpensive, robust process to reduce the amount of hemicellulose in livestock feed.

Prior work on hydrolysis of biomass materials has focused on recovering all or nearly all of the carbohydrate value from the biomass material, including glucose from hydrolysis of the cellulose fraction of the biomass material. For example, U.S. Pat. No. 4,752,579 to Arena et al., discloses subjecting corn kernel hulls to acid hydrolysis at a temperature of 35 to 110° C. and then treating the acid hydrolysis reaction product with cellulose-degrading enzyme to complete the hydrolysis of the unreacted cellulose. The initial acid hydrolysis is said to produce a liquid portion that includes monosaccharides (chiefly D-glucose, D-xylose and L-arabinose). Arena et al., also state that the acid hydrolysis reaction product may be separated into liquid and solid portions prior to subjecting the solids portion to enzymatic hydrolysis. Similarly, U.S. Pat. No. 5,628,830 to Brink discloses hydrolyzing a biomass material under conditions to hydrolyze the hemicellulose content without substantial hydrolysis of the cellulosic content, then subjecting residual solid biomass to enzymatic hydrolysis to convert the cellulose to glucose. U.S. Pat. No. 5,536,325 to Brink discloses a non-enzymatic hydrolysis that involves subjecting a biomass material to a first stage hydrolysis at 140–220° C. and pH of 2.0–3.0 to cause hydrolysis of the hemicellulose, contacting the resultant intermediate with air at 140–220° C., followed by a second stage hydrolysis at 160–240° C.

SUMMARY OF THE INVENTION

The present invention provides for selective hydrolysis of the hemicellulose component of a biomass material. The selective hydrolysis produces water-soluble small molecules, particularly monosaccharides that can serve as precursors to higher value chemicals. In particular, the method converts at least a portion of the hemicellulose component of the biomass material into an aqueous product stream that is rich in monosaccharides. The method additionally reduces the quantity of residual water insoluble biosolids requiring further processing or disposal.

According to a first embodiment of the invention, there is provided a method for hydrolyzing hemicellulose present in a biomass material comprising solubilizing at least a portion of the hemicellulose and subsequently hydrolyzing the solubilized hemicellulose to produce at least one monosaccharide.

According to a second embodiment of the invention, there is provided a method for hydrolyzing hemicellulose present in a biomass material comprising solubilizing at least a portion of the hemicellulose and subsequently enzymatically hydrolyzing the solubilized hemicellulose to produce at least one monosaccharide.

According to a third embodiment of the invention, there is provided a method for hydrolyzing hemicellulose in a biomass material comprising solubilizing at least a portion of the hemicellulose by heating the biomass material to greater than 110° C. resulting in a water insoluble solids fraction and an aqueous fraction that includes the solubilized hemicellulose and subsequently separating the aqueous fraction from the water insoluble solids fraction.

A further advantage of the invention is that the solubilized hemicellulose is easily separated from the water insoluble solid components of the biomass material such as cellulose and protein. Such solid portion can be used as an improved livestock feed since it includes a lower amount of hemicellulose than conventional livestock feed. In particular, according to a fourth embodiment of the invention there is provided a method for making a composition that includes cellulose, at least one protein and less than about 30 weight %, hemicellulose, the method comprising solubilizing at least a portion of hemicellulose present in a biomass material that also includes cellulose and at least one protein and subsequently separating the solubilized hemicellulose from the cellulose and at least one protein.

The hydrolysis conditions described below in more detail for hydrolyzing the hemicellulose are milder (e.g., lower temperature, less acid) than those necessary to hydrolyze cellulose. Moreover, valuable monomers such as monosaccharides are rapidly hydrolyzed at the conditions for hydrolyzing cellulose. Thus, the present methods provide for hydrolyzation of the hemicellulose with no or only nominal hydrolyzation of the cellulose.

DETAILED DESCRIPTION OF PREFERRED EMBODIMENTS

The biomass material may be any cellulosic material that includes hemicellulose. Such materials include plant fiber and wood fiber. The process is especially effective with grain fibers such as corn, wheat, rice, oats or barley. The biomass material can be byproducts and waste generated from agricultural or food processing. One type of biomass material that is particularly suitable for use with the invention is corn fiber.

Preferably, an aqueous slurry of raw or pretreated biomass material is utilized as the starting material for all embodiments of the invention. The aqueous slurry may be prepared by any conventional means such as by simply mixing the biomass material with water. The amount of water used in the slurry is not critical and can vary widely. For example, the weight % of biomass material mixed in the water can range from about 5 to 30.

The hydrolysis of the biomass material according to all embodiments of the invention results in at least two product fractions or streams. One product fraction is an aqueous composition that includes water-soluble monosaccharides as the primary component (i.e., the highest amount component other than water). The aqueous product fraction may also possibly include residual disaccharides or oligosaccharides. The other product fraction is a mixture of water insoluble (at room temperature) solids, primarily cellulose and protein. In other words, cellulose and protein are substantially non-hydrolyzed by the inventive methods.

Illustrative monosaccharides in the aqueous product stream are pentoses (for example, xylose and arabinose) and hexoses (for example, glucose, mannose and galactose). In the instance of corn fiber as the biomass material, xylose and arabinose are present in the highest amounts in the aqueous product stream. The present invention may be sufficiently efficient for producing monosaccharides in an amount of at least about 60%, preferably about 80%, of the monosaccharides theoretically available in the hemicellulose and starch present in the starting biomass material.

The monosaccharides present in the aqueous product stream can be converted via known techniques into higher value products. Especially useful are the $C_5$ monosaccharides derived from corn fiber. These monosaccharides can be used as feedstocks for downstream processing such as catalytic processing to produce chemicals such as polyols (e.g., ethylene glycol, propylene glycol or glycerol) or fermentation to produce ethanol.

The solids product fraction is useful as an improved livestock feed since it includes a smaller amount of hemicellulose. The solids product fraction may include less than about 30 weight %, preferably less than about 20 weight %, and more preferably less than about 10 weight % hemicellulose, based on the total amount of hemicellulose, cellulose and protein. The solids product fraction may also be further processed to recover other valued constituents, including glucose, protein and other organic compounds. It has also been found that the residual water insoluble solids are produced in the form of a fine particulate as a consequence of the methods of the invention. The finer particle distribution of the residual water insoluble solids improves the accessibility to the constituents in this stream.

The particular process embodiments summarized above are described in more detail below.

The first embodiment includes two distinct steps—solubilization followed by hydrolysis. By performing these two steps, formation of undesirable dehydration byproducts is minimized and conversion of soluble polysaccharides to monomers is maximized. In addition, the initial hemicellulose solubilization step in the first embodiment results in a convenient water-soluble portion that can then easily undergo targeted hemicellulose hydrolyzation in the second step.

The hemicellulose solubilization in the first embodiment usually involves heating the biomass material. This solubilizing step preferably is performed under reaction conditions sufficient to convert at least a portion of the initial hemicellulose fraction into smaller oligomeric fractions that are substantially water-soluble. At least a portion of any starch and/or protein also present in the biomass material may similarly undergo conversion into smaller oligomeric, water-soluble fractions. A portion of the hemicellulose (and starch if present) may be hydrolyzed to monosaccharides or disaccharides during the solubilizing step. The reaction conditions may be maintained to achieve the desired amount of solubilization while limiting the amount of monosaccharides dehydrated to byproducts such as furfural. Such byproducts may lead to undesirable products for downstream processing. For example, in the instance of corn fiber starting material about 20 to 80, preferably about 40 to 60, weight % of the corn fiber may be solubilized (based on the total amount of the corn fiber).

During the solubilizing step the biomass material typically is subjected to a temperature of about 110 to 220, preferably about 120 to 160° C. Optionally, acid may be added to the biomass material to assist in the solubilizing step. Sufficient acid may be added so that the pH of the reactant mixture ranges from about 1 to 3, preferably about 2 to 3. Typically, about 1 to 3 weight % (based on the total weight of biomass material) of acid is added. Examples of suitable acids include acetic, sulfuric, nitric, hydrochloric, phosphoric and carbonic acid. Sulfuric and nitric acid are preferred. If acid is not utilized, the pH of the reactant mixture may range from about 3.5 to 5. The temperature for performing the solubilizing typically can be lowered if an acid is used. For example, the more preferred range with an acid is about 120 to 140° C. and the more preferred range without an acid is about 140 to 160° C. The reaction time for the solubilizing varies depending upon the heating temperature and the presence or absence of an acid. For example, if an acid is present and the reaction temperature is about 120 to 140° C., the solubilizing step is maintained for about 10 to 60 minutes. If an acid is not present and the reaction temperature is about 140 to 160° C., the solubilizing step is maintained for about 30 to 90 minutes. The solubilizing reaction pressure is not critical.

The second step of the first embodiment involves further hydrolyzing the solubilized hemicellulose to produce at least one monosaccharide. This second step serves to hydrolyze the oligomeric fragments remaining from the solubilization. In general, at least the aqueous hemicellulose-containing intermediate product fraction from the solubilizing step is subjected to a second set of hydrolysis reaction conditions. One example of such hydrolysis conditions is a thermochemical hydrolysis.

During the second step the solubilization step product (or solubilized hemicellulose-containing fraction thereof) typically is subjected to a temperature of less than 160° C., usually about 120 to 150 and preferably 120 to 140° C. Preferably, acid is added in the second step to promote the hydrolysis. Sufficient acid may be added so that the pH of the reactant mixture ranges from about 1 to 3, preferably about 1.5 to 2.5. Examples of suitable acids include acetic, sulfuric, nitric, hydrochloric, phosphoric and carbonic acid. Sulfuric and nitric acid are preferred. The reaction time for the second step varies depending upon the heating temperature and the pH. For example, the reaction time may be about 10 to 120 minutes.

The first embodiment may also include at least one optional separation step between the solubilizing step and the subsequent hydrolysis step. According to one separation variant, the liquid solubilized hemicellulose-containing fraction is separated from the water insoluble solid fraction. Separation may be accomplished by any known liquid/solid separation technique such as membrane separation, filtration or centrifugation. The separated solubilized hemicellulose-containing fraction is then subjected to the subsequent hydrolysis step. A second separation variant involves removing monosaccharides generated from the solubilizing step. In particular, the solubilizing step product mixture may be subjected to filtration or membrane separation for removing a portion of the monosaccharides. Removing the monosaccharides after the solubilizing step minimizes the formation of degradation products and maximizes monosaccharide production during the subsequent hydrolysis step.

The second embodiment includes two distinct steps—solubilization followed by hydrolysis. By performing these two steps, formation of undesirable dehydration byproducts is minimized and conversion of soluble polysaccharides to monomers is maximized. In addition, the initial hemicellulose solubilization step in the second embodiment results in a convenient water-soluble portion that can then easily undergo targeted hemicellulose hydrolyzation in the second step.

The hemicellulose solubilization step in the second embodiment usually involves heating the biomass material. The solubilizing step preferably is performed under reaction conditions sufficient to convert at least a portion of the initial hemicellulose fraction into smaller oligomeric fractions that are substantially water-soluble. At least a portion of any starch and/or protein also present in the biomass material may similarly undergo conversion into smaller oligomeric, water-soluble, fractions. A portion of the hemicellulose (and starch if present) may be hydrolyzed to monosaccharides or disaccharides during the solubilizing step. The reaction conditions may be maintained to achieve the desired amount of solubilization while limiting the amount of monosaccharides dehydrated to byproducts such as furfural. Such byproducts may lead to undesirable products for downstream processing. For example, in the instance of corn fiber starting material about 20 to 80, preferably about 40 to 60, weight % of the corn fiber may be solubilized (based on the total amount of the corn fiber).

During the solubilizing step the biomass material typically is subjected to a temperature of about 100 to 220, preferably 135 to 160° C. Optionally, acid may be added to the biomass material to assist in the solubilizing step. Sufficient acid may be added so that the pH of the reactant mixture ranges from about 1 to 3, preferably about 1.5 to 2.5. Typically, about 1 to 3 weight % (based on the total weight of biomass material) of acid is added. Examples of suitable acids include acetic, sulfuric, nitric, hydrochloric, phosphoric and carbonic acid. Sulfuric and nitric acid are preferred. If acid is not utilized, the pH of the reactant mixture ranges from about 3.5 to 5. The temperature for performing the solubilizing typically can be lowered if an acid is used. For example, the more preferred range with an acid is about 120 to 140° C. and the more preferred range without an acid is about 140 to 160° C. The reaction time for the solubilizing varies depending upon the heating temperature and the presence or absence of an acid. For example, if an acid is present and the reaction temperature is about 120 to 140° C., the solubilizing step is maintained for about 10 to 60 minutes. If an acid is not present and the reaction temperature is about 140 to 160° C., the solubilizing is maintained for about 30 to 90 minutes.

The second step in the second embodiment involves enzymatically hydrolyzing the solubilized hemicellulose intermediate products to produce at least one monosaccharide. The enzymatic step hydrolyzes a substantial portion of the higher carbon hydrolyzable constituents present in the solubilized hemicellulose fraction. Such higher carbon hydrolyzable constituents may include solubilized polymeric and oligomeric saccharide fragments and disaccharides.

The enzyme(s) may be added to the total solubilizing step product mixture (i.e., both the liquid and solid fractions). The enzyme(s) is selected so that they will hydrolyze the solubilized hemicellulose components and starch without also hydrolyzing any meaningful amount of the cellulose. Alternatively, the liquid solubilized hemicellulose-containing fraction is separated from the water insoluble solid fraction. Separation may be accomplished by any known liquid/solid separation technique such as membrane separation, filtration or centrifugation. The separated solubilized hemicellulose-containing fraction then is subjected to the subsequent enzymatic hydrolysis step.

A single enzyme or a mixture of enzymes may be utilized. Suitable enzyme(s) are those that have hydrolytic reactivity for complex and various structures (such as the arabinoxylan structure) within hemicellulose. Illustrative enzyme mixtures that are relatively inexpensive include xylanase (commercially available from GNC Bioferm, Inc. of Saskatchewan, Canada), maizase (commercially available from Biotal Canada Limited of Ontario, Canada) and silase (commercially available from Biotal Canada Limited of Ontario, Canada). The amount of enzyme added may vary and typically is dependent upon the reaction temperature and pH.

During the second step the enzyme(s) is added to the solubilizing step product (or solubilized hemicellulose-containing fraction thereof) and the resulting mixture typically is subjected to a temperature of about 30 to 70, preferably 40 to 60° C. Preferably, acid or base is also added in the second step to promote the hydrolysis. The acid or base may be added prior to the addition of the enzyme(s) so that the appropriate pH conditions exist for the enzymes. Sufficient acid or base may be added so that the pH of the reactant mixture ranges from about 3.0 to 5.5, preferably about 3.5 to 5. Examples of suitable acids include acetic, sulfuric, nitric, hydrochloric, phosphoric and carbonic acid. Examples of suitable bases include sodium hydroxide and calcium hydroxide. The reaction time for the second step varies depending upon the heating temperature and the pH.

The third embodiment of the invention is a one-step hydrolysis of the biomass material to solubilize the hemicellulose so that it can be easily separated from the water insoluble solids. The biomass material is heated to greater than 110° C. so that a sufficient amount of hemicellulose is solubilized into an aqueous product stream. In general, the one-step hydrolysis is performed at greater than 110° C. to about 200° C., preferably about 120 to 160° C. Optionally, acid may be added to the biomass material to assist in the hydrolysis step. Sufficient acid may be added so that the pH of the reactant mixture ranges from about 1 to 3. Typically, about 1 to 3 weight % (based on the total weight of biomass material) of acid is added. Examples of suitable acids include acetic, sulfuric, nitric, hydrochloric, phosphoric and carbonic acid. If acid is not utilized, the pH of the reactant mixture ranges from about 3.5 to 5. The temperature for performing the hydrolysis typically can be lowered if an acid is used. For example, the more preferred range with an acid is about 120 to 140° C. and the more preferred range without an acid is about 140 to 160° C. The reaction time for the one-step hydrolysis varies depending upon the heating temperature and the presence or absence of an acid. For example, if an acid is present and the reaction temperature is about 120 to 140° C., the hydrolysis is maintained for about 10 to 60 minutes. If an acid is not present and the reaction temperature is about 140 to 160° C., the hydrolysis is maintained for about 30 to 90 minutes.

After the one-step hydrolysis is completed, the resulting monosaccharide-rich aqueous fraction is separated from the residual water insoluble solids fraction via known liquid/solid separation techniques. Illustrative separation processes include membrane separation or filtration.

As described above, the fourth embodiment of the invention includes solubilizing at least a portion of hemicellulose present in a biomass material that also includes cellulose and at least one protein. The hemicellulose solubilization can be accomplished by any of the processes described above in connection with the other embodiments. The separation step in the fourth embodiment can be accomplished via any suitable technique for separating a liquid from a solid such as membrane separation or filtration.

All the processes of the invention can be performed as continuous operations and/or batch processes in any suitable reactor equipment. For example, in the two step first and second embodiments a continuous plug flow reactor may be employed. The reactor could include a first section for performing an autogenous (i.e., no acid) solubilization, a second section for decreasing the temperature via a cooler, a third section for adding/mixing the acid with a static mixer, followed by a fourth section for performing the hydrolyzation step. The specific reactor atmospheric and pressure conditions may vary.

The specific examples described below are for illustrative purposes and should not be considered as limiting the scope of this invention.

EXAMPLE 1

An aqueous slurry of corn fiber is prepared by mixing 12.5 g of corn fiber and 87.5 g of water. The slurry is then fed into a reactor vessel and heated for 60 minutes at about 150° C. and a pH of about 4.6. The resulting intermediate product mixture is cooled to room temperature. Subsequently, the intermediate product mixture is mixed with 0.2 g of sulfuric acid and then fed into a reactor vessel and heated for 90 minutes at about 120° C. Actual quantification analysis of the product from this example was not performed, but it is expected that the resulting product comprises an aqueous fraction that should include approximately 4 weight % of the various monosaccharides and a water insoluble solids fraction that includes only about 50 weight % of the mass of the starting corn fiber material (i.e., about 50 weight % of the corn fiber was solubilized). It is also expected that the water insoluble solids include less 10 weight % hemicellulose. This expected monosaccharide amount in the aqueous fraction indicates approximately 80% conversion of the initial hemicellulose in the corn fiber starting material. The amount of residual cellulose in the solids fraction is substantially the same as the amount of cellulose in the corn fiber starting material indicating substantially no hydrolysis of the cellulose.

These expected quantification numbers are extrapolated from two actual data sets. In one set, only the solubilization step described in this Example 1 was performed (60 minutes, 150° C., pH 4.6) and the resulting aqueous fraction included about 2 weight % monosaccharides. In another set, only the subsequent hydrolysis step described in this Example was performed (90 minutes, 120° C., acid) and the resulting aqueous fraction included about 2.5 weight % monosaccharides. The combination of the two steps should significantly increase the amount of monosaccharides.

EXAMPLE 2

An aqueous slurry of corn fiber is prepared by mixing 12.5 g of corn fiber and 87.5 g of water. The slurry is and then fed into a reactor vessel and heated for 60 minutes at about 150° C. and a pH of about 4.6. The resulting intermediate product mixture is cooled to room temperature. Subsequently, the intermediate product mixture is adjusted to a pH of about 4.5, mixed with xylanase and then fed into a reactor vessel and heated for 8 hours at about 50° C. and a pH of 4.5. This process was repeated with maizase and silase.

Actual quantification analysis of the product from this example was not performed, but it is expected that the resulting product comprises an aqueous fraction that should include approximately 4 weight % of the various monosaccharides and a water insoluble solids fraction that includes only about 50 weight % of the mass of the starting corn fiber material (i.e., about 50 weight % of the corn fiber was solubilized). It is also expected that the water insoluble solids include less 10 weight % hemicellulose. This expected monosaccharide amount in the aqueous fraction indicates approximately 80% conversion of the initial hemicellulose in the corn fiber starting material. The amount of residual cellulose in the solids fraction is substantially the same as the amount of cellulose in the corn fiber starting material indicating substantially no hydrolysis of the cellulose.

These expected quantification numbers are extrapolated from actual data obtained by performing enzymatic hydrolysis directly on "raw" corn fiber (i.e., corn fiber that was not subjected to the initial solubilization step). The direct enzymatic hydrolysis was performed by mixing 100 mg maizase, 137 mg xylanase and 106 mg silase with an aqueous corn fiber slurry (12.5 weight % corn fiber) and then heating the resulting mixture at 50° C. and a pH of 4 for 8 hours. Approximately 30 weight % of the corn fiber was solubilized. The aqueous product stream included about 4.4 weight % of the various monosaccharides and approximately 100% of the solubilized corn fiber was converted to monosaccharides.

EXAMPLE 3

An aqueous slurry of corn fiber is prepared by mixing 12.5 g of corn fiber and 87.5 g of water. The slurry is mixed with 0.125 g of nitric acid and then fed into a reactor vessel and heated for 60 minutes at about 150° C. and a pH of about 2.8. The resulting product mixture is cooled to room temperature and then separated via filtration into an aqueous fraction that includes about 2 weight % monosaccharides and a water insoluble solids fraction that includes that only includes about 50 weight % of the mass of starting corn fiber material (i.e., approximately 50 weight % of the fiber was solubilized). The water insoluble solids include less then 10 weight percent hemicellulose. The monosaccharide amount in the aqueous fraction indicates approximately 50% conversion of the initial hemicellulose in the corn fiber starting material. The amount of residual cellulose in the solids fraction is substantially the same as the amount of cellulose in the corn fiber starting material indicating substantially no hydrolysis of the cellulose.

Having illustrated and described the principles of our invention with reference to several preferred embodiments, it should be apparent to those of ordinary skill in the art that the invention may be modified in arrangement and detail without departing from such principles.

What is claimed is:

1. A method for hydrolyzing hemicellulose in a biomass material comprising:
   (a) solubilizing at least a portion of the hemicellulose in the presence of an acid and subsequently
   (b) hydrolyzing the solubilized hemicellulose to produce at least one monosaccharide.

2. A method according to claim 1 wherein step (a) comprises heating the biomass material at about 110 to about 220° C.

3. A method according to claim 1 wherein step (a) further comprises heating the biomass material at about 120 to about 140° C.

4. A method for hydrolyzing hemicellulose in a biomass material comprising:
   (a) solubilizing at least a portion of the hemicellulose in the presence of an acid and subsequently
   (b) enzymatically hydrolyzing the solubilized hemicellulose to produce at least one monosaccharide.

5. A method according to claim 4 wherein step (a) comprises heating the biomass material at about 100 to about 220° C.

6. A method according to claim 4 further comprising adding a base or second acid in step (b).

7. A method according to claim 4 wherein step (b) comprises contacting the solubilized with at least one enzyme selected from xylanase, maizase and silase.

8. A method according to claim 4 wherein the product resulting from step (b) comprises (i) an aqueous fraction that includes at least one monosaccharide and (ii) a water insoluble solids fraction that includes cellulose.

9. A method according to claim 4 wherein the biomass material comprises corn fiber.

10. A method for hydrolyzing hemicellulose in a biomass material comprising:
    (a) solubilizing at least a portion of the hemicellulose by heating the biomass material to greater than 110° C. in the presence of an acid resulting in an aqueous fraction that includes the solubilized hemicellulose and a water insoluble solids fraction and subsequently
    (b) separating the aqueous fraction from the water insoluble solids fraction.

11. A method for hydrolyzing hemicellulose in a biomass material comprising:
    (a) solubilizing at least a portion of the hemicellulose in the presence of a first acid and subsequently
    (b) hydrolyzing the solubilized hemicellulose in the presence of a second acid to produce at least one monosaccharide.

12. A method according to claim 11 wherein substantially no cellulose is hydrolyzed in steps (a) and (b).

13. A method for hydrolyzing hemicellulose in a biomass material that also includes cellulose comprising:
    (a) solubilizing at least a portion of the hemicellulose resulting in (i) an aqueous fraction that includes the solubilized hemicellulose and (ii) a water insoluble fraction that includes cellulose and subsequently
    (b) hydrolyzing the solubilized hemicellulose in the presence of the cellulose to produce at least one monosaccharide,
    wherein substantially no cellulose is hydrolyzed in steps (a) and (b).

14. A method for hydrolyzing hemicellulose in a biomass material that also includes cellulose comprising:
    (a) solubilizing at least a portion of the hemicellulose resulting in (i) an aqueous fraction that includes the solubilized hemicellulose and (ii) a water insoluble fraction that includes cellulose and subsequently
    (b) enzymatically hydrolyzing the solubilized hemicellulose in the presence of the cellulose to produce at least one monosaccharide,
    wherein substantially no cellulose is hydrolyzed in steps (a) and (b).

15. A method according to claim 14 wherein step (b) comprises contacting the solubilized hemicellulose with at least one enzyme selected from xylanase, maizase and silase.

16. A method according to claim 14 further comprising adding an acid in at least one of steps (a) and (b).

17. A method for hydrolyzing hemicellulose in a biomass material comprising:
    (a) solubilizing at least a portion of the hemicellulose by heating the biomass material to greater than 110° C. in the presence of an acid resulting in an aqueous fraction that includes the solubilized hemicellulose and at least one monosaccharide, and a water insoluble solids fraction and subsequently
    (b) separating the aqueous fraction from the water insoluble solids fraction wherein substantially no cellulose is hydrolyzed in steps (a) and (b).

18. A method for hydrolyzing hemicellulose in a biomass material comprising:
    (a) solubilizing at least a portion of the hemicellulose to produce (i) a first aqueous fraction that includes solubilized hemicellulose and (ii) a water insoluble solids fraction that includes cellulose
    (b) hydrolyzing the solubilized hemicellulose to produce a product comprising a second aqueous fraction that includes at least one monosaccharide and
    (c) separating the second aqueous fraction from the water insoluble solids fraction.

19. A method for hydrolyzing hemicellulose in corn fiber comprising:
    (a) forming an aqueous slurry of corn fiber
    (b) heating the aqueous slurry of corn fiber to a temperature of about 120 to about 160° C. in the absence of an acid to produce a water insoluble solids fraction that includes cellulose and an aqueous fraction that includes solubilized hemicellulose and substantially no hydrolyzed cellulose,
    (c) separating the aqueous fraction from the water insoluble solids fraction and subsequently
    (d) hydrolyzing the solubilized hemicellulose-containing aqueous fraction in the presence of an acid.

20. A method for hydrolyzing hemicellulose in corn fiber comprising:
    (a) heating the corn fiber at a temperature of about 120° C. to about 140° C. so as to solubilize about 40 to about 80 weight percent of the corn fiber such that at least a portion of the hemicellulose is solubilized and subsequently
    (b) hydrolyzing the solubilized hemicellulose to produce at least one monosaccharide.

* * * * *